United States Patent [19]

Niwa

[11] Patent Number: 5,238,000
[45] Date of Patent: Aug. 24, 1993

[54] PULSE WAVE DETECTING APPARATUS
[75] Inventor: Minoru Niwa, Nagoya, Japan
[73] Assignee: Colin Electronics Co., Ltd., Aichi, Japan
[21] Appl. No.: 752,016
[22] Filed: Aug. 29, 1991
[30] Foreign Application Priority Data Sep. 10, 1990 [JP] Japan .................... 2-95433[U]

[51] Int. Cl.$^5$ ............................................ A61B 5/022
[52] U.S. Cl. ................................. 128/689; 128/690; 128/672
[58] Field of Search ................... 128/672, 680, 687–690
[56] References Cited

U.S. PATENT DOCUMENTS

| | | | |
|---|---|---|---|
| 2,555,422 | 6/1951 | Scott et al. | 128/672 |
| 3,102,534 | 9/1963 | Bigliano et al. | 128/672 |
| 3,219,035 | 11/1965 | Pressman et al. | 128/672 |
| 3,738,356 | 6/1973 | Workman | 128/672 |
| 4,475,554 | 10/1984 | Hyndman | 128/664 |
| 4,658,829 | 4/1987 | Wallace | 128/672 |
| 4,784,152 | 11/1988 | Shinoda et al. | 128/690 |
| 4,799,491 | 1/1989 | Eckerle | 128/672 |
| 4,802,488 | 2/1989 | Eckerle | 128/672 |
| 4,830,017 | 5/1989 | Perry et al. | 128/672 |
| 4,832,039 | 5/1989 | Perry et al. | 128/680 |
| 4,836,213 | 6/1989 | Wenzel et al. | 128/672 |
| 4,901,733 | 2/1990 | Kaida et al. | 128/687 |
| 4,924,871 | 5/1990 | Honeyager | 128/672 |
| 4,947,855 | 8/1990 | Yokoe et al. | 128/672 |
| 4,951,679 | 8/1990 | Harada | 128/672 |
| 4,966,156 | 10/1990 | Perry et al. | 128/672 |
| 4,987,900 | 1/1991 | Eckerle et al. | 128/672 |

FOREIGN PATENT DOCUMENTS

| | | | |
|---|---|---|---|
| 0326384 | 8/1989 | European Pat. Off. | 128/672 |
| 0326385 | 8/1989 | European Pat. Off. | 128/687 |
| 0330434 | 8/1989 | European Pat. Off. | 128/690 |
| 0334652 | 9/1989 | European Pat. Off. | 128/672 |
| 0337591 | 10/1989 | European Pat. Off. | 128/689 |
| 63-293424 | 11/1988 | Japan. | |
| 2-79904 | 6/1990 | Japan. | |
| 90/02512 | 3/1990 | World Int. Prop. O. | |

OTHER PUBLICATIONS

Tochikubo et al., "Measurements of Base Blood Pressure During Sleep and Its Clinical etc.", Jap. Cir. Journ., vol. 51, Oct. 1987.

Primary Examiner—Lee S. Cohen
Assistant Examiner—Jeffrey R. Jastrzab
Attorney, Agent, or Firm—Oliff & Berridge

[57] ABSTRACT

An apparatus for detecting a pressure pulse wave produced from an artery of a living subject, including a first press member having a first press surface, a pressure sensing device supported by the first press surface, a second press member having a second press surface surrounding the first press surface, a pressing device pressing the first and second press members toward a body surface of the subject so that the first press surface is pressed against the artery via the body surface, the pressure sensing device generating an electric signal representing the pressure pulse wave produced from the artery and transmitted thereto via the body surface, the first and second press members being displaceable relative to each other in a direction in which the first and second press members are pressed by the pressing device, an actuating device displacing the first press member relative to the second press member so that the first press surface is advanced outward from the second press surface, and a determining device determining an optimum amount of the outward advance of the first press surface from the second press surface, by utilizing the electric signal generated from the pressure sensing device when the first press member is displaced outward from the second press member by the actuating device with the second press member being pressed on the body surface by the pressing device.

20 Claims, 5 Drawing Sheets

PULSE WAVE DETECTING APPARATUS

BACKGROUND OF THE INVENTION

1. Field of the Invention

The present invention generally relates to a pulse wave detecting apparatus and particularly to such an apparatus which is capable of changing the outward advance amount of a first press surface in which a pressure sensing device is provided, from a second press surface surrounding the first press surface.

2. Related Art Statement

The Assignee of the present U.S. patent application had filed a Japanese utility model application, which was published under Publication No. 2-79904 on Jun. 20, 1990, which discloses an apparatus for detecting a pressure pulse wave produced from an artery of a living subject, including (a) a first press member having a first press surface, (b) a pressure sensing device supported by the first press surface, (c) a second press member having a second press surface surrounding the first press surface, (d) a pressing device pressing the first and second press members toward a body surface of the subject so that the first press surface is pressed against the artery of the subject via the body surface, the pressure sensing device generating an electric signal representing the pressure pulse wave produced from the artery and transmitted thereto via the body surface, the first and second press members being displaceable relative to each other in a direction in which the first and second press members are pressed by the pressing device, and (e) an actuating device displacing the first press member relative to the second press member so that the first press surface is advanced outward from the second press surface.

In the case where an artery from which the above apparatus is to detect pressure pulse wave is located at a small depth from the body surface on which the apparatus is set, the actuating device holds the first press surface at a small outward advance amount from the second press surface while the pressing device presses the second press member on the body surface. Thus, the apparatus is free from the problem that because of, for example, physical motion of the subject, the first press member may be tilted with respect to the artery while the first press member is pressed on the body surface. In this respect, the apparatus stably detects the pressure pulse wave. Meanwhile, in the case where the artery is located at a large depth from the body surface, the apparatus stably detects the pressure pulse wave by holding the first press surface at a large outward advance amount from the second press surface, without having to press the second press surface so strongly as the first press surface. Accordingly, the apparatus is free from the problem that the second press surface is pressed strongly against the bone or tendon of the subject, preventing the subject from feeling discomfort due to the strong pressing.

However, the above apparatus is adapted to determine an optimum pressing force of the pressing device at which the pressure sensing device detects the pressure pulse wave, by pressing both the first and second press members against the body surface and, if the determined optimum pressing force is greater than a reference value, retracting the second press member relative to the first press member, such that these operations are repeated until a determined optimum pressing force becomes not greater than the reference value. If the determined optimum pressing force is greater than the reference value, the apparatus gives the subject some discomfort since the second press member is pressed for some time against the body surface together with the first press member at a force greater than the optimum pressing force. In addition, if the pressing and retracting operations are repeated many times, the subject feels much discomfort. Thus, the above apparatus is not satisfactory.

SUMMARY OF THE INVENTION

It is therefore an object of the present invention to provide a pulse wave detecting apparatus which is capable of determining an optimum outward advance amount of the first press surface from the second press surface, based on the pressure pulse wave (e.g., amplitude and/or lower peak magnitude) detected through the pressure sensing device while the first press member is displaced outward from the second press member by the actuating device with the second press member being pressed on the body surface by the pressing device.

The above object has been achieved by the present invention, which provides an apparatus for detecting a pressure pulse wave produced from an arterial vessel of a living subject, comprising (a) a first press member having a first press surface, (b) pressure sensing means supported by the first press surface, (c) a second press member having a second press surface surrounding the first press surface, (d) pressing means for pressing the first and second press members toward a body surface of the subject so that the first press surface is pressed against the arterial vessel of the subject via the body surface, the pressure sensing means generating an electric signal representing the pressure pulse wave produced from the arterial vessel and transmitted thereto via the body surface, the first and second press members being displaceable relative to each other in a direction in which the first and second press members are pressed by the pressing means, (e) actuating means for displacing the first press member relative to the second press member so that the first press surface is advanced outward from the second press surface, and (f) determining means for determining an optimum amount of the outward advance of the first press surface from the second press surface, by utilizing the electric signal generated from the pressure sensing means when the first press member is displaced outward from the second press member by the actuating means with the second press member being pressed on the body surface by the pressing means.

In the pulse wave detecting apparatus constructed as described above, the actuating means displaces the first press member relative to the second press member pressed on the body surface by the pressing means so that the first press surface is advanced outward from the second press surface, and the determining means determines an optimum amount of the outward advance of the first press surface from the second press surface, by utilizing the electric signal generated from the pressure sensing means while the first press member is displaced outward from the second press member by the actuating means with the second press surface being pressed on the body surface. Therefore, the present apparatus is free from the problem that the second press member is strongly pressed on the body surface, one or more times, together with the first press member for determining the optimum advance amount therefor, thereby relieving the subject from discomfort otherwise resulting from the strong pressing.

According to a feature of the present invention, the pulse wave detecting apparatus further comprising adjusting means for determining a pulse rate of the subject by utilizing the electric signal generated from the pressure sensing means and adjusting, by utilizing the determined pulse rate, a rate of the outward advance of the first press surface for the determination of the optimum outward advance amount. Provided that the rate of outward advance of the first press surface is constant irrespective of different pulse rates of a subject or subjects, only an insufficient number of pulses of the pressure pulse wave are obtained from a subject whose pulse rate is relatively low, during the outward advance of the first press surface for the determination of the optimum outward advance amount therefor. Consequently, the resolution or number of sample data for determining the optimum advance amount is reduced, so that the optimum advance amount may not be determined with satisfactory accuracy. According to this feature of the present invention, however, the rate of the outward advance of the first press surface is adjusted based on the pulse rate of the subject, and therefore the number of pulses of the pressure pulse wave detected during the outward advance of the first press member is not reduced even for a subject having a low pulse rate. Thus, good resolution or sufficient number of sample data is obtained, which contributes to determine the optimum outward advance amount of the first press surface with high accuracy.

According to another feature of the present invention, the adjusting means determines as the pulse rate a time duration, t, of a pulse of the pressure pulse wave represented by the electric signal from the pressure sensing means, and adjusts the outward advance rate to a value, a/t (a; constant).

According to yet another feature of the present invention, the adjusting means determines as the pulse rate a time duration, t, of each of pulses of the pressure pulse wave detected through the pressure sensing means during the outward advance of the first press surface for the determination of the optimum advance amount, and adjusts the outward advance rate to a value, at (a; constant), for detecting the pulse following each pulse.

According to a further feature of the present invention, the pressing means presses the first press member on the body surface at a predetermined pressure level during the outward advance of the first pressure surface for the determination of the optimum advance amount.

In a preferred embodiment of the present invention, the determining means (a) collects the electric signal corresponding to a plurality of pulses of the pressure pulse wave while the first press surface is advanced outward from the second press surface; (b) determines a lower peak magnitude and an amplitude of each of the pulses; (c) determines a first range of the outward advance amount of the first press surface in which range a change of the amplitude with respect to the outward advance amount is within a first predetermined value and which range contains an advance amount at which the pressure sensing means has detected a pulse having a maximum amplitude of the amplitudes of the pulses, and a second range of the outward advance amount in which range a change of the lower peak magnitude with respect to the outward advance amount is within a second predetermined value; and (d) determines the optimum outward advance amount based on the first and second ranges. In this case, the determining means may determine as the optimum outward advance amount (a) an outward advance amount corresponding to the middle point of the second range in the case where the first range contains the second range in entirety thereof; (b), in the case where the first and second ranges partially overlap each other, an outward advance amount corresponding to the middle point of the overlapping portions of the first and second ranges; and (c) an outward advance amount corresponding to the middle point of the first range in the case where the second range contains the first range in entirety thereof or in the case where the first and second ranges are separate from each other.

In another embodiment of the present invention, the determining means (a) collects the electric signal corresponding to a plurality of pulses of the pressure pulse wave while the first press surface is advanced outward from the second press surface; (b) determines an amplitude of each of the pulses; and (c) determines as the optimum outward advance amount an outward advance amount at which the pressure sensing means has detected a pulse having a maximum amplitude of the amplitudes of the pulses.

In yet another embodiment of the present invention, the actuating means ceases advancing the first press surface upon determination of the optimum outward advance amount.

In a further embodiment of the present invention, the pressure sensing means comprises a plurality of pressure sensing elements each of which detects the pressure pulse wave and generates an electric signal representing the detected pressure pulse wave, the determining means determining an amplitude of each of pulses of the pressure pulse wave detected through the each pressure sensing element, selecting as an optimum pressure sensing element one of the pressure sensing elements which has detected a pulse having a maximum amplitude of the amplitudes determined for the elements, and determining the optimum advance amount by utilizing the electric signal supplied from the optimum pressure sensing element.

According to a feature of the present invention, the apparatus further comprises blood pressure determining means for identifying an upper and a lower peak of each of pulses of the pressure pulse wave represented by the electric signal from the pressure sensing means, and determining a systolic and a diastolic blood pressure of the subject based on the identified upper and lower peaks, respectively, for the each pulse. In this case, the apparatus may further comprise displaying means for indicating a waveform of the pressure pulse wave detected by the pressure sensing means, and the systolic and diastolic blood pressure values determined by the blood pressure determining means.

According to another feature of the present invention, the actuating means comprises means for defining a fluid chamber, and means for supplying the fluid chamber with a pressurized, non-compressible fluid for displacing the first press member relative to the second press member.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
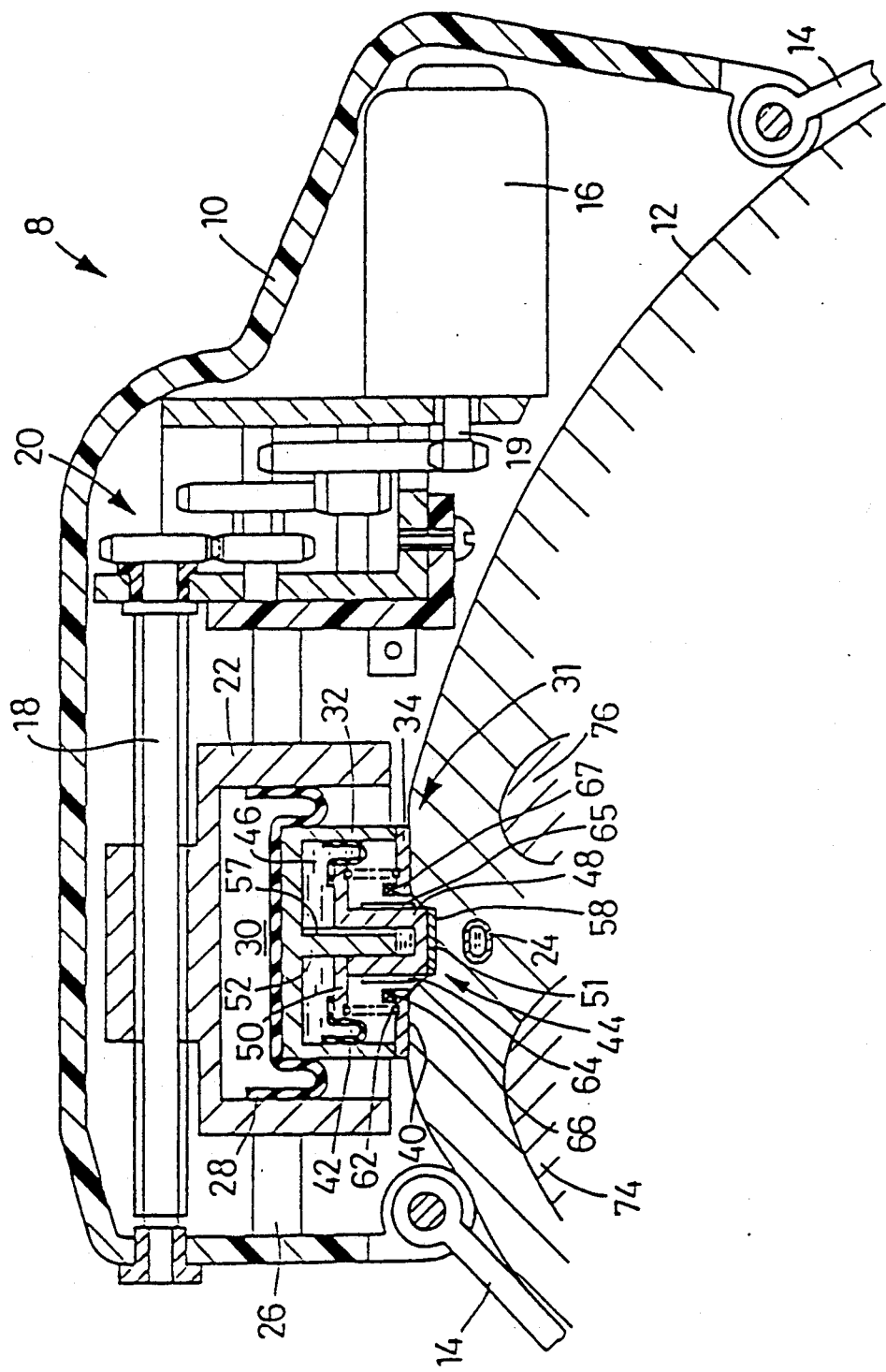
FIG. 1 is a sectional view of a detector probe constituting a part of a pulse wave detecting apparatus to which the present invention is applied, the probe being set on a living subject.

Referring first to FIG. 1, there is shown a detector probe 8 constituting a part of a pulse wave detecting apparatus embodying the present invention. The detector probe 8 includes a housing 10 having a container-like configuration as a whole. The housing 10 is detachably set on a body surface 12 of a wrist of a living subject with the help of fastening bands 14, 14, such that the open end of the housing 10 contacts the body surface 12.

The housing 10 accommodates a drive motor 16, a feed screw 18, a reduction gear unit 20 operatively connecting between an output shaft 19 of the drive motor 16 and one of axially opposite ends of the feed screw 18, and a cylindrical member 22 having a bottom wall which is held in threaded engagement with the feed screw 18. With the probe 8 being set on the wrist, the feed screw 18 is driven or rotated by the drive motor 16, so that the cylindrical member 22 is moved in a direction substantially perpendicular to an artery 24 below the body surface 12 of the wrist. The cylindrical member 22 has a pair of straight guide grooves (not shown) in outer side surfaces thereof which are opposite to each other and parallel to the feed screw 18. The guide grooves engage a pair of straight guide rails 26, 26 (only one rail 26 is shown in FIG. 1) which are formed in inner wall surfaces of the housing 10. The cylindrical member 22 is guided by the engaged straight guide groove and rails 26, 26 over a predetermined distance or stroke without rattling.

Figure 2:
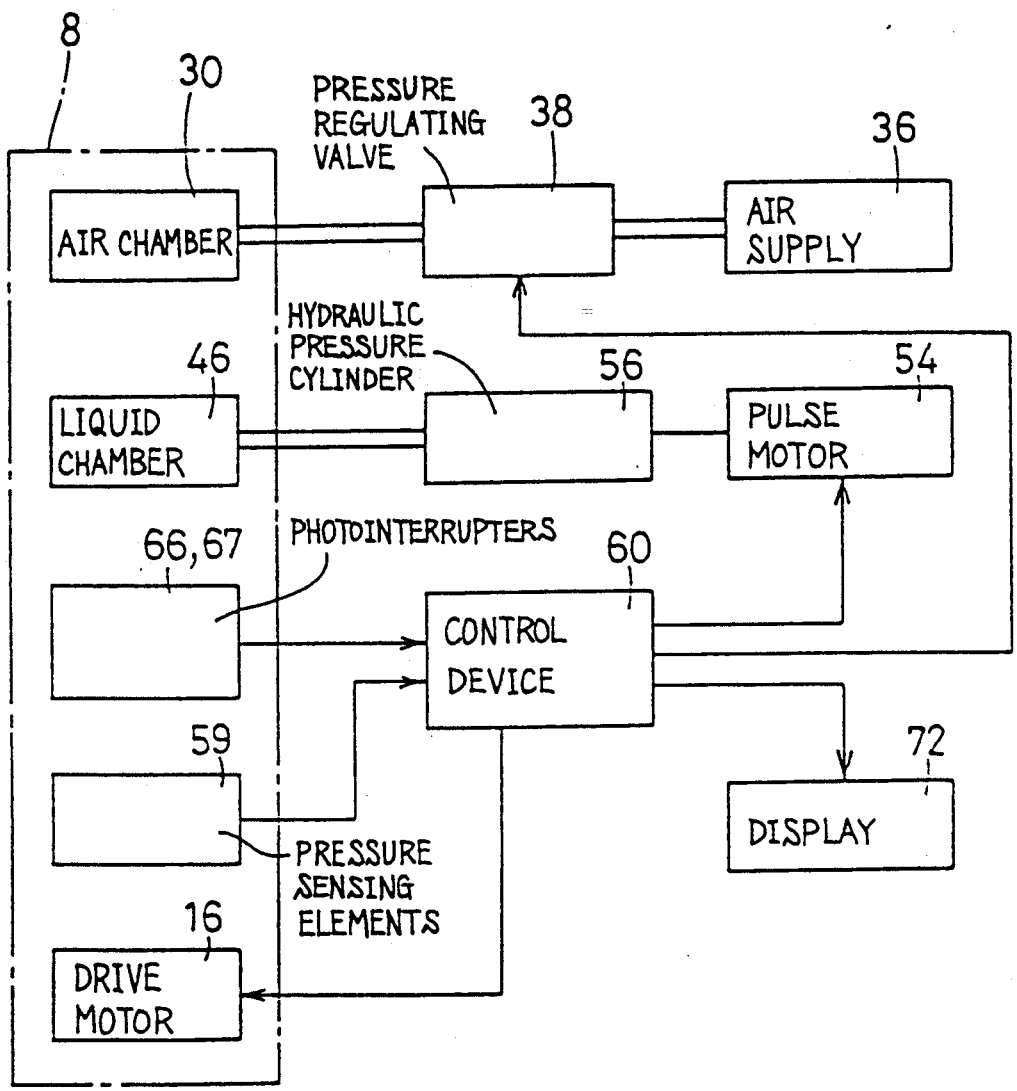
FIG. 2 is a diagrammatic view for illustrating the construction of the pulse wave detecting apparatus.

An elastic diaphragm 28 is secured to the inner wall of the cylindrical member 22. The diaphragm 28 cooperates with the bottom wall of the cylindrical member 22 to define an air chamber 30. To a central portion of one of opposite surfaces of the diaphragm 28 which one surface is different from the other surface defining the air chamber 30, a press member 31 is secured. The press member 31 has a container-like configuration as a whole, and includes a cylindrical casing 32 secured at the bottom wall thereof to the diaphragm 28, and an annular plate 34 fixed to the open end of the casing 32. The annular plate 34 has a press surface 40. As illustrated in FIG. 2, the air chamber 30 is supplied with pressurized air from an air supply 36 via a pressure regulating valve 38. When the diaphragm 28 is inflated, namely, air pressure in the air chamber 30 is increased, the press surface 40 is pressed on the body surface 12 with a force corresponding to the air pressure in the chamber 30.

A pulse wave sensor 44 is secured to the inner wall of the press member 31 or casing 32 via an elastic diaphragm 42, such that the sensor 44 is displaceable relative to the press member 31. The sensor 44, diaphragm 42, and bottom wall of the casing 32 cooperate with each other to define a liquid chamber 46 whose volume is variable. The pulse wave sensor 44 includes a cylindrical portion 48 having a bottom wall, a flange portion 50 extending outwardly from an open end of the cylindrical portion 48, and a semiconductor substrate 51 fixed to the outer surface of the bottom wall of the cylindrical portion 48. The substrate 51 has a press surface 58. The cylindrical portion 48 of the sensor 44 engages a cylindrical support portion 52 extending from a center of the bottom wall of the casing 32, such that the cylindrical portion 48 is advanceable out of, and retractable into, the casing 32 through the annular member 34, so that the cylindrical portion 48 or semiconductor substrate 51 is moved toward or away from the body surface 12 or artery 24.

As illustrated in FIG. 2, the liquid chamber 46 is supplied with pressurized liquid, such as silicone oil, from a hydraulic pressure cylinder 56 which is actuated by a pulse motor 54. When the volume of the liquid chamber 46 is increased as a result of flowing thereinto of the pressurized fluid, the cylindrical portion 48 of the pulse wave sensor 44, that is, the press surface 58 of the semiconductor substrate 51 (hereinafter, referred to as the "first press surface") is advanced out of the level of the press surface 40 of the press member 31 (hereinafter, referred to as the "second press surface"), so that the first press surface 58 is pressed on the body surface 12. In the present embodiment, the pulse wave sensor 44 serves as the first press member having the first press surface 58, while the press member 31 serves as the second press member having the second press surface 40 surrounding the first press surface 58. In addition, the air chamber 30, air supply 36, and pressure regulating valve 38 cooperate with each other to serve as the pressing means for pressing the first and second press members 44, 31 as a unit toward the body surface 12 so that the first press surface 58 is pressed against the artery 24 via the body surface 12. Further, the liquid chamber 46, pulse motor 54 and hydraulic pressure cylinder 56 cooperate with each other to serve as the actuating means for displacing the first press member 44 relative to the second press member 31 so that the first press surface 58 is advanced outward from the second press surface 40.

The cylindrical support portion 52 of the press member 31 has a plurality of grooves 57 (only one groove is shown in FIG. 1) equiangularly formed in the outer circumferential surface thereof. The grooves 57 extend axially of the support portion 52 and open in a free end of the same 52. Through the grooves 57, liquid is fed from the liquid chamber 56 to a space temporarily provided between the bottom of the cylindrical portion 48 of the sensor 44 and the free end of the support portion 52 of the press member 31.

The semiconductor substrate 51 of the pulse wave sensor 44 includes, in the first press surface 58, a multiplicity of pressure sensing elements 59 (FIG. 2) such as pressure sensing diodes or semiconductor strain gauges. The pressure sensing elements 59 are arranged in an array parallel to the feed screw 18, so that the array of elements 59 extends in a direction perpendicular to the artery 24. An example of such an array of pressure sensing elements is disclosed in Japanese Patent Application laid open under Publication No. 63(1988)-293424, which was filed by the Assignee of the present U.S. patent application. With the semiconductor substrate 51 or first press surface 58 being pressed against the artery 24 via the body surface 12, each of the pressure sensing elements 59 detects a pressure pulse wave produced from the artery in synchronism with heartbeat of the subject and transmitted thereto via the body surface 12, and generates an electric signal representing the detected pulse wave to a control device 60.

Between the flange portion 50 of the pulse wave sensor 44 and the annular plate 34 of the press member 31, there is disposed a compression coil spring 62. When the hydraulic pressure cylinder 56 is actuated by the pulse motor 56 in a direction to remove the fluid from the fluid chamber 56, the pulse wave sensor 44 is moved into the press member 31 because of a biasing force of the coil spring 62, to a retracted position thereof in which the bottom of the cylindrical portion 48 of the sensor 44 engages the free end of the support portion 52 of the press member 31 and in which the first press surface 58 is aligned with the second press surface 40.

In the present embodiment, there is also provided a sensing device for detecting that the pulse wave sensor (first press member) 44 is located in the retracted position thereof and detecting that the sensor 44 is located in a predetermined limit (or maximum) advanced position thereof in which the first press surface 58 is remote from the first press surface 40 by, for example, about 3 to 4 mm. This sensing device includes a pair of reflection plates 64, 65 and a pair of photointerrupters 66, 67. The two reflection plates 64, 65 are fixed to the outer circumferential surface of the cylindrical portion 48 of the pulse wave sensor 44, such that the reflections plates 64, 65 are opposite to each other diametrically of the cylindrical portion 48. The two photointerrupters 66, 67 are secured to the inner surface of the annular plate 34 opposite to the second press surface 40, such that the interrupters 66, 67 are located radially inwardly of the compression coil spring 62 and are opposed to the corresponding reflection plates 64, 65. The first reflection plate 64 includes a light-reflecting area of a small length in one of opposite end portions thereof which one end portion (i.e., lower end portion as seen in FIG. 1) is located on the side of the first press surface 58. The remaining or other area of the first reflection plate 64 is a non-reflection area which does not reflect light incident thereto. Meanwhile, the second reflection plate 65 includes a light-reflecting area of a small length in one of opposite end portions thereof which one end portion (i.e., upper end portion as seen in FIG. 1) is located on the side of the flange portion 50. The remaining area of the second reflection plate 65 is a non-reflection area. Each of the photointerrupters 66, 67 generates an electric signal to the control device 60, when each interrupter 66, 67 receives, from the corresponding reflection plate (or light-reflecting area thereof) 64, 65, the reflected light of an intensity greater than a reference value. Generation of the electric signal from the first photointerrupter 66 corresponding to the first reflection plate 64, means that the first press surface 58 is located in the retracted position thereof, while generation of the electric signal from the second photointerrupter 67 corresponding to the second reflection plate 65, means that the first press surface 58 is located in the limit advanced position thereof. In FIG. 1, reference numerals 74 and 76 denote a bone (radius) and a tendon, respectively.

The control device 60 includes a microcomputer constituted by a central processing unit (CPU), a read only memory (ROM), a random access memory (RAM), an input and output interface, and others. The CPU processes input signals according to various programs pre-stored in the ROM by utilizing the temporary-storage function of the RAM, so as to control the operations of the drive motor 16 and pressure regulating valve 38 and thereby locate the pulse wave sensor 44 directly above the artery 24, and control the operation of the pressure regulating valve 38 and thereby hold the air pressure in the air chamber 30 at a predetermined value, at which the second press surface 40 is pressed on the body surface 12. With the second press surface 40 being pressed, and becoming stationary, on the body surface 12, the CPU operates to control, according to a program pre-stored in the ROM, the operation of the pulse motor 54 and thereby advance the first press surface 58 outward from the second press surface 40 at a rate of displacement depending upon a pulse rate of the subject. The control device 60 collects the electric signals supplied from the pressure sensing elements 59 while the first press surface 58 is advanced outward from the second press surface 40, and selects, based on the pressure pulse waves represented by the collected electric signals, an optimum pressure sensing element 59 out of the multiplicity of pressure sensing elements 59 and an optimum amount of the outward advance of the first press surface 58 from the second press surface 40. The ROM pre-stores a predetermined pulse number necessary for the pulse motor 54 to advance the pulse wave sensor 44 from the retracted position thereof to the limit advanced position thereof. By adjusting the number of pulses supplied to the pulse motor 54, the control device 60 accurately adjusts the amount of outward advance, in increments, of the first press surface 58 from the second press surface 40.

Further, the CPU operates to control, according a program pre-stored in the ROM, the operation of a display 72 such as a cathode ray tube (CRT) and thereby indicate on the display 72 the waveform of the pressure pulse wave represented by the electric signal supplied from the optimum pressure sensing element 59 with the first press surface 58 being located at the optimum outward advance amount from the second press surface 40. Based on the obtained waveform, the control device 60 determines a systolic and a diastolic blood pressure of the subject, and the display 72 indicates the determined blood pressure values. It is however possible depending upon particular applications of the present apparatus that the display 72 be adapted to indicate only one of the waveform and the blood pressure values. In addition, it is possible to record the waveform and/or the blood pressure values on a chart or record sheet in addition to, or in place of, indication on the display 72.

Figure 3A:
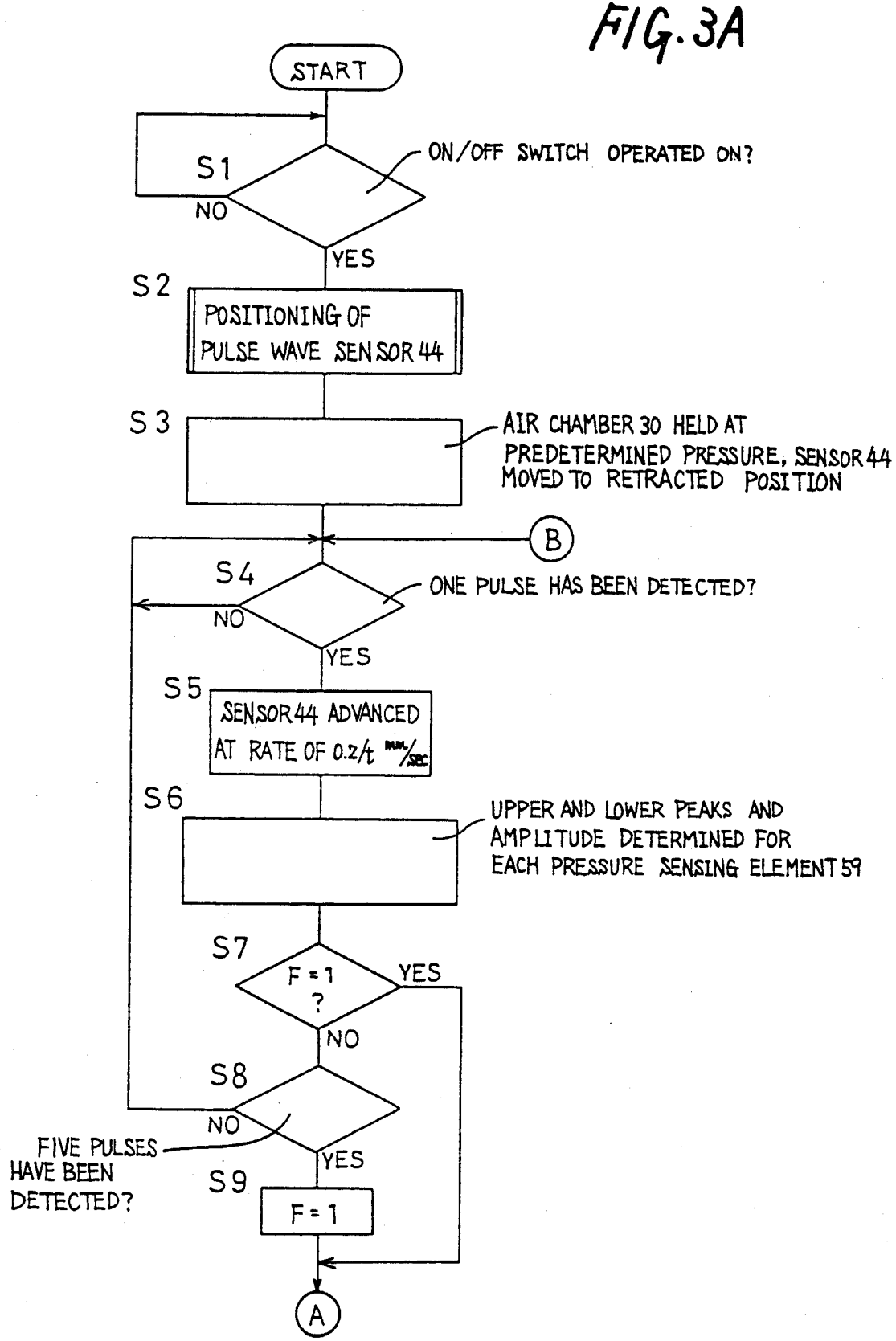
FIGS. 3A and 3B are a flow chart for explaining the operation of the pulse wave detecting apparatus of FIG. 2.
Figure 3B:
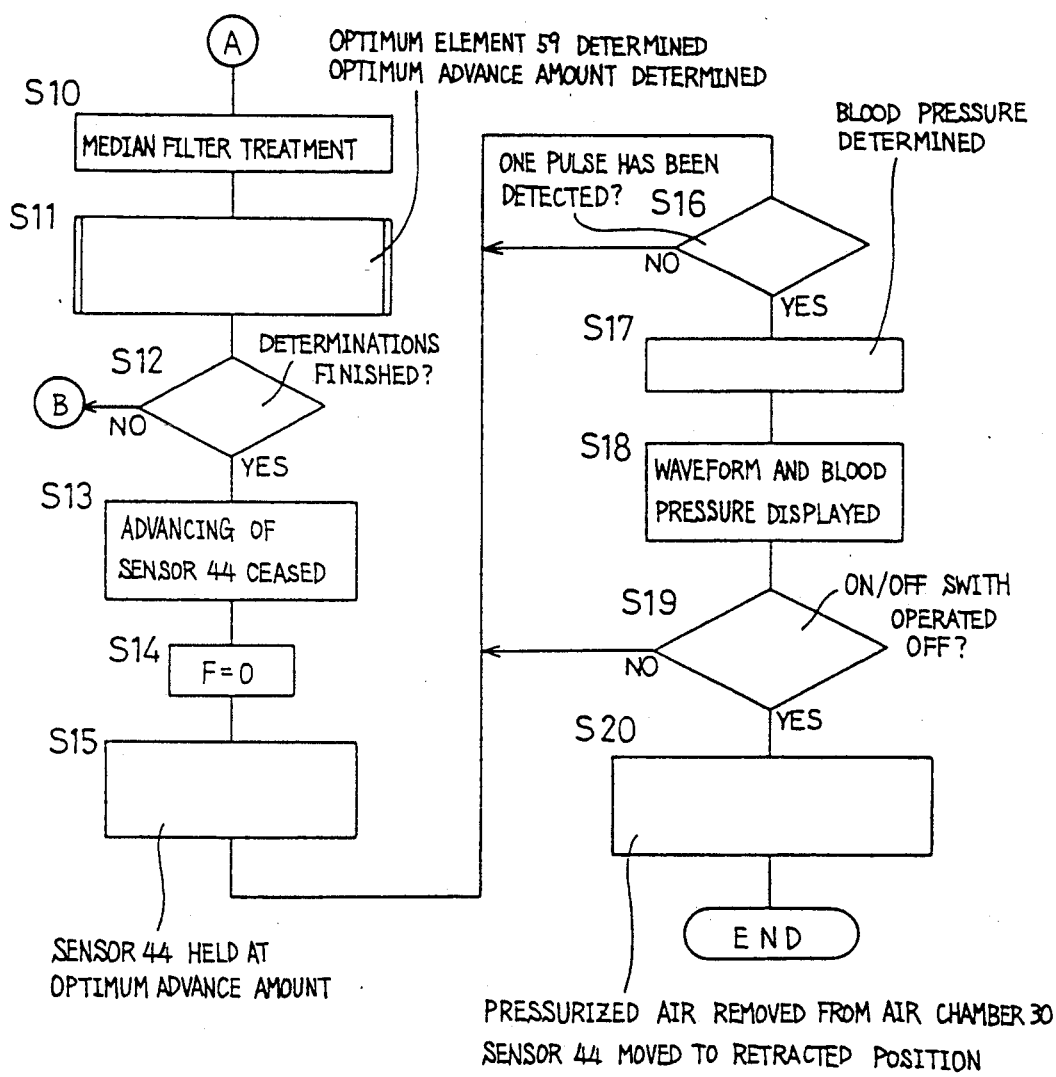

Next, there will be described the operation of the pulse wave detecting apparatus constructed as described above, by reference to the flow chart of FIG. 3.

Upon application of electric power to the apparatus with the detector probe 8 being set on the wrist 12 of a subject, the CPU of the control device 60 first effects initialization of the apparatus, subsequently the control of the CPU proceeds with Step S1 to identify whether or not an ON/OFF switch (not shown) has been operated to an ON position thereof. In the case where a negative judgement (NO) is made in Step S1, the CPU repeats Step S1. Meanwhile, if an affirmative judgement (YES) is made in Step S1, the control goes to Step S2 to actuate the pulse motor 54 and thereby advance the first press surface 58 outward from the second press surface 40 by about 1 mm and concurrently control the pressure regulating valve 38 to increase and hold the air pressure in the air chamber 30 to and at a predetermined value (e.g., about 50 mmHg). In this condition, the control device 60 collects the electric signals fed from the pressure sensing elements 59 supported by the first press surface 58 pressed on the body surface 12, and judges, based on the pressure pulse waves represented by the collected electric signals, whether or not the array of pressure sensing elements 59 is positioned such that the artery 24 is below the middle portion of the array of elements 59. If a negative judgement is made, the control device 60 actuates the drive motor 16 and thereby displaces the pulse wave sensor 44 in increments in the direction perpendicular to the artery 24. For each incremental displacement of the sensor 44, the control device 60 repeats the pressing of the sensor 44 onto the body surface 12 and the above described judging operation. If an affirmative judgement is made, that means that the sensor 44 is located in the position where the artery 24 is below the middle portion of the array of pressure sensing elements 59. In this situation, the distribution in magnitude of the electric signals from the individual elements 59 of the array defines a curve having a plateau in the middle portion thereof as viewed along the array.

After the pulse wave sensor 44 is thus located in position in Step S2, the control of the CPU goes to Step S3 to retract the sensor 44 to the retracted position thereof with the air pressure in the chamber 30 being maintained at the above-indicated predetermined value. Step S3 is followed by Step S4 to identify whether or not the control device 60 has collected an electric signal corresponding to one pulse, i.e., one heartbeat of the subject, from each of the pressure sensing elements 59. If an negative judgement is made in Step S4, the CPU repeats Step S4. Meanwhile, if an affirmative judgement is made in Step S4, the control goes to Step S5 to calculate a time duration, t sec, needed for detection of the one pulse, determine a rate of the outward advance of the first press surface 58 by dividing 0.2 mm by t sec, and start advancing the first press surface 58 outward from the second press surface 40 at the rate of 0.2/t mm/sec. The time duration t corresponds to a pulse rate of the subject.

Step S5 is followed by Step S6 to determine, for each pressure sensing element 59, the magnitudes of upper and lower peaks of the one pulse collected therefrom in Step S4 and additionally determines the magnitude of an amplitude of the one pulse based on the magnitudes of the upper and lower peaks. The magnitudes of lower peaks and amplitudes are stored in the RAM, in association with the corresponding pressure sensing elements 59.

Subsequently, the control of the CPU proceeds to Step S7 to identify whether or not a flag, F, is held in a position thereof, F=1. If the flag is in the position F=1, that indicates that the control device 60 has collected from the pressure sensing elements 59 the electric signals corresponding to 5 pulses after the outward advance of the pulse wave sensor 44 or first press surface 58 has started. Step S7 is followed by Step S8 to judge whether or not the control device 60 has collected from the elements 59 the electric signals corresponding to 5 pulses after the starting of the outward advance of the pulse wave sensor 44. In the case where a negative judgement is made in Step S8, the CPU repeats Step S4 through Step S8.

If the control device 60 has collected from the elements 59 the electric signals corresponding to 5 pulses and therefore an affirmative judgement is made in Step S8, the control of the CPU goes to Step S9 to place the flag in the position thereof F=1 and subsequently to Step S10. In Step S10, for each of the pressure sensing elements 59, a group of the magnitudes or values of the five lower peaks and a group of the values of the five amplitudes each are subjected to median filter treatment (one of well-known statistical treatments). Specifically, the time-wise third values of the five lower peaks and five amplitudes are replaced with the third largest values of the same, and the third largest lower peak magnitude and amplitude are selected for each pressure sensing element 59.

Figure 4:
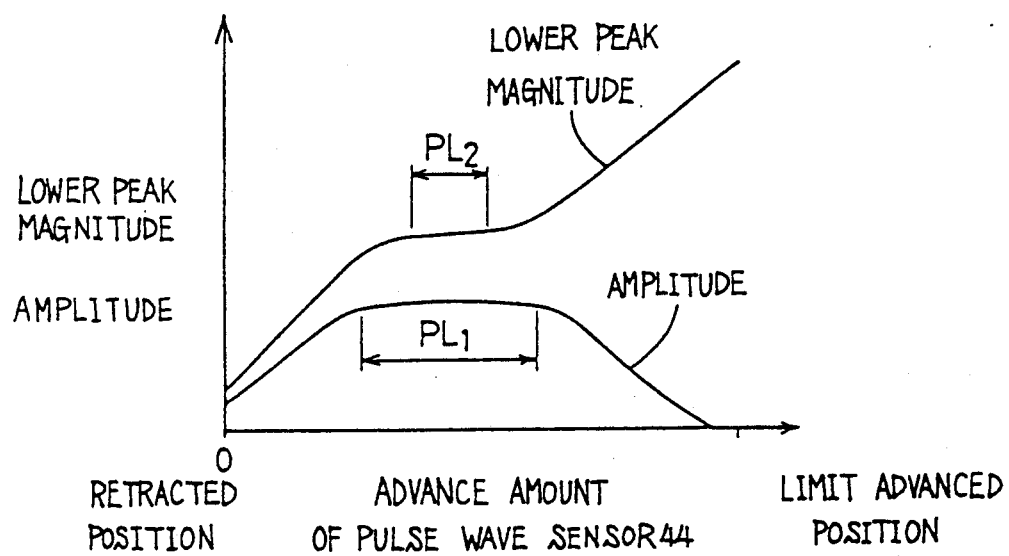
FIG. 4 is a graph showing exemplary curves respectively representing variations of the amplitude and lower peak magnitude of the pressure pulse wave detected by the optimum pressure sensing element during advancing of the pulse wave sensor when the apparatus is operated according to the flow chart of FIGS. 3A and 3B.

Step S10 is followed by Step S11 to determine as an optimum pressure sensing element 59 one of the elements 59 which, during the outward advance of the pulse wave sensor 44, has supplied an electric signal or pressure pulse wave whose amplitude is the greatest of the amplitudes selected for all the elements 59. In addition, the control device 60 determines, on a curve (FIG. 4) representing variation in the amplitudes of the five pulses detected through the optimum element 59, a specific range, $PL_1$, of the outward advance amount of the pulse wave sensor 44, in which range a change in the amplitude with respect to the outward advance amount of the sensor 44 is within a predetermined value and which range contains a particular advance amount at which the optimum element 59 has detected a pulse having the greatest amplitude of the amplitudes of the five pulses. The particular advance amount corresponds to a point at which the rate of change of the amplitude with respect to the outward advance amount of the sensor 44 is zero. For example, the range $PL_1$ may be determined such that the difference between the greatest amplitude and each of the other amplitudes in the range $PL_1$ is smaller than a considerably small value, for example, 7 mmHg in terms of pressure. Also, the control device 60 determines, on another curve (FIG. 4) representing variation in the lower peak magnitudes of the five pulses detected through the optimum element 59, another specific range, $PL_2$, of the outward advance amount of the pulse wave sensor 44, in which range a change in the lower peak magnitudes with respect to the outward advance amount of the sensor 44 is within a predetermined value (e.g., 7 mmHg in terms of pressure). The range $PL_2$ may be determined such that the range $PL_2$ includes a point at which the rate of change of the amplitude with respect to the outward advance amount of the sensor 44 is minimum and that the difference between a selected one of the lower peak values in the range $PL_2$ and each of the other lower peak values is smaller than a considerably small value, for example, 7 mmHg in terms of pressure. Based on the first and second ranges $PL_1$ and $PL_2$, the control device 60 determines an optimum amount of the outward advance of the pulse wave sensor 44 from the press member 31. More specifically described, in the case where the second range $PL_2$ falls in its entirety within the first range $PL_1$, as is the case with FIG. 4, the control device 60 determines as the optimum advance amount an advance amount corresponding to the middle point of the second range $PL_2$. In the case where the first and second ranges $PL_1$, $PL_2$ partially overlap each other, the control device 60 determines as the optimum advance amount an advance amount corresponding to the middle point of the overlapping portions of the first and second ranges $PL_1$, $PL_2$. In the case where the first range $PL_1$ falls in its entirety within the second range $PL_2$, or in the case where the first and second ranges $PL_1$, $PL_2$ do not overlap each other, that is, are separate from each other, the control device 60 determines as the optimum advance amount an advance amount corresponding to the middle point of the first range $PL_1$. In the present embodiment, Step S11 and the microcomputer for effecting Step S11 serve as the determining means for determining the optimum amount of the outward advance of the first press surface 58 from the second press surface 40. The two curves shown in FIG. 4 indicate respective variations in the amplitudes and the lower peak magnitudes of the five pulses provided that the pulse wave sensor 44 is advanced to the limit advanced position thereof.

Step S11 is followed by Step S12 to judge whether or not both the optimum pressure sensing element 59 and the optimum outward advance amount have been determined. In the case where a negative judgement is made in Step S12, the control of the CPU goes back to Step S4 and the following steps, so that the outward advance of the pulse wave sensor 44 further continues while the rate of the outward advance is adjusted in Step S5 each time one pulse of the pressure pulse wave is detected in Step S4, and that the various operations are effected for determining the optimum pressure sensing element 59 and the optimum outward advance amount of the sensor 44. In the present embodiment, Step S5 and the microcomputer for effecting Step S5 serve as the adjusting means for determining a pulse rate of the subject and adjusting the rate of the outward advance of the first press surface 58 based on the determined pulse rate. While Step S4 through Step S12 are repeated, an affirmative judgement is made in Step S7 and therefore Steps S8 and S9 are skipped, so that Step S7 is followed by Step S10.

If an affirmative judgement is made in Step S12, the control of the CPU goes to Step S13 to deactivate the pulse motor 54 and thereby stop the outward advance of the pulse wave sensor 44, and subsequently to Step S14 to reset the flag to a position thereof, F=0 Step S14 is followed by Step S15 to actuate the pulse motor 54 so as to hold the first press surface 58 at the optimum outward advance amount from the second press surface 40. In Step S15, after the sensor 44 has been retracted to the retracted position thereof, the sensor 44 is advanced by the optimum amount by the pulse motor 54 being driven by a number of pulses corresponding to the optimum amount.

With the pulse wave sensor 44 or first press surface 58 being held at the optimum advance amount from the second press surface 40, the control of the CPU goes to Step S16 to identify whether or not the optimum pressure sensing element 59 has supplied an electric signal corresponding to one pulse of the pressure pulse wave. If an affirmative judgement is made in Step S16, the control goes to Step S17 to determine systolic and diastolic blood pressure values of the subject based on the upper and lower peak magnitudes of the detected one pulse, according to a well-known algorithm pre-stored in the ROM. Step S17 is followed by Step S18 to indicate on the display 72 the waveform of the pressure pulse wave (one pulse) detected in Step S16 and the blood pressure values determined in Step S17.

Subsequently, the control of the CPU goes to Step S19 to identify whether or not the ON/OFF switch has been operated to an OFF position thereof. In the case where a negative judgement is made in Step S19, the CPU repeats Steps S16 through S19 to display the waveform and blood pressure values for each of successive pulses of the pressure pulse wave. On the other hand, if an affirmative judgement is made in Step S19, the control goes to Step S20 to remove the pressurized air from the air chamber 30 and retract the pulse wave sensor 44 to the retracted position thereof. The operation of the present apparatus is thus ended.

In the pulse wave detecting apparatus constructed and arranged as described above, an optimum outward advance amount of the pulse wave sensor 44 or first press surface 58 is determined by advancing the first press surface 58 from the second press surface 40 with the press member 31 or second press surface 40 being fixed on the body surface 12. While the first press surface 58 is advanced outward from the second press surface 40 for the determination of the optimum outward advance amount, the rate of the outward advance is adjusted depending upon a current pulse rate of the subject. Accordingly, a sufficient number of pulses of the pressure pulse wave for accurately determining the optimum advance amount of the sensor 44 are obtained from even a subject whose pulse rate is relatively low. In other words, an amplitude-advance amount relationship curve and a lower peak magnitude-advance amount relationship curve are obtained with good resolution or sufficient number of sample data, and an optimum advance amount of the sensor 44 is determined with high accuracy.

In addition, the present apparatus is adapted to adjust the rate of advance of the pulse wave sensor 44 for each pulse of the pressure pulse wave. Therefore, even in the case where the pulse rate of the subject is unexpectedly reduced during advancing of the sensor 44, a sufficient number of pulses of the pressure pulse wave, that is, sufficient number of sample data are obtained.

Further, since the present apparatus is adapted to cease advancing the pulse wave sensor 44 upon determination of the optimum advance amount therefor and subsequently hold the sensor 44 or first press surface 58 at the determined optimum advance amount from the press member 31 or second press surface, the apparatus gives the subject only a reduced pain as compared with the case where the sensor 44 might be advanced to the limit advanced position thereof. For the same reason, the apparatus provides another advantage of starting detection of the pressure pulse wave very quickly with the sensor 44 being positioned at the optimum advance amount thereof.

In the present apparatus, the pulse wave sensor 44 is actuated to advance toward the body surface 12, by the pressure of the liquid supplied to the liquid chamber 46 in response to operation of the pulse motor 54. The amount of advance of the sensor 44 is linearly regulated by the number of pulses applied to the pulse motor 54, and therefore the rate of advance of the sensor 44 is adjusted with high accuracy. As compared with the case where the optimum advance amount of the sensor 44 is maintained by utilizing air (or air pressure), the present apparatus more stably holds the sensor 44 at the optimum advance distance, thereby detecting pressure pulse wave with higher reliability.

While the present invention has been described in its presently preferred embodiment, it is to be understood that the present invention may otherwise be embodied.

For example, although, in the illustrated embodiment, advancing of the pulse wave sensor 44 is stopped upon determination of the optimum advance amount therefor, it is possible to determine the optimum advance amount based on the pressure pulse wave detected while the sensor 44 is advanced up to the limit advanced position thereof.

In addition, while in the illustrated embodiment the rate of advance of the pulse wave sensor 44 is adjusted based on each pulse at the time the each pulse is detected during advancing of the sensor 44, it is possible to adjust the advance rate for every two or three pulses, or adjust the advance rate based on the pressure pulse wave detected before advancing of the sensor 44.

In the illustrated embodiment, the optimum advance amount of the pulse wave sensor 44 is determined by utilizing the first and second ranges $PL_1$, $PL_2$ determined on the amplitude and lower peak magnitude variation curves obtained using the optimum pressure sensing element 59. However, it is possible to utilize as the optimum advance amount an advance amount of the sensor 44 at which the optimum element 59 has detected a pulse having a maximum amplitude of all the amplitudes detected during advancing of the sensor 44. Since a sufficient number of pulses of the pressure pulse wave, i.e., sufficient number of sample data are obtained, an amplitude variation curve is obtained with satisfactory resolution, and an optimum advance amount of the sensor 44 is determined with high accuracy.

Although in the illustrated embodiment the air pressure in the air chamber 30 is maintained at a predetermined value for the determination of the optimum pressure sensing element and/or optimum advance amount of the pulse wave sensor 44, it is possible to provide the apparatus with means for changing the air pressure at which the air chamber 30 is maintained.

While the illustrated apparatus is adapted to displace the pulse wave sensor 44 by means of the hydraulic pressure cylinder actuated by the pulse motor 54, it is possible to adapt the apparatus such that the sensor 44 is driven directly by a motor.

In place of the pulse motor 54 used to actuate the hydraulic pressure cylinder 56 in the illustrated embodiment, it is possible to employ the combination of a direct current motor and a rotary encoder to operate the cylinder 56. Even in this case, the advance amount of the sensor 44 accurately is regulated in small increments.

In addition, while in the illustrated embodiment the combination of reflection plates 64, 65 and photointerrupters 66, 67 are used for detecting the retracted and limit advanced positions of the pulse wave sensor 44, different means such as a proximity switch, microswitch, or pressure sensor for detecting a pressure in the liquid chamber 46 may be employed for the same purpose.

Although in the illustrated embodiment the pulse wave sensor 44 includes a multiplicity of pressure sensing elements 59, it is possible to detect the pressure pulse wave by using a single pressure sensing element.

In the illustrated embodiment, the detector probe has the positioning device, including the drive motor 16, reduction gear unit 20, and feed screw 18, for locating the pulse wave sensor 44 in position in the direction perpendicular to the artery 24. However, it is possible to omit the positioning device without adversely affecting the important operations of the apparatus.

It is to be understood that the present invention may be embodied with other changes, improvements and modifications that may occur to those skilled in the art without departing from the scope and spirit of the invention defined in the appended claims.

What is claimed is:

1. An apparatus for detecting a pressure pulse wave produced from an arterial vessel of a living subject, comprising:

a housing;

fastening means connected to said housing, for fastening said housing on a body portion of said subject, said fastening means comprising at least one band which is adapted to be wound around said body portion;

a press member including a first press portion having a first press surface, and a second press portion having a second press surface surrounding said first press surface;

pressure sensing means supported by said first press surface;

pressing means disposed between said housing and said press member, for pressing said press member toward a body surface of said subject so that said first press surface is pressed against said arterial vessel of said subject via said body surface;

said pressure sensing means generating an electric signal representing said pressure pulse wave produced from said arterial vessel and transmitted thereto via said body surface;

said first and second press portions being displaceable relative to each other in a direction in which said press member is pressed by said pressing means;

actuating means for displacing said first press portion relative to said second press portion so that said first press surface is advanced outward from said second press surface; and determining means for determining an optimum amount of the outward advance of said first press surface from said second press surface, by utilizing the electric signal generated by said pressure sensing means when said first press portion is displaced outward from said second press portion by said actuating means with said press member being pressed on said body surface by said pressing means, said pressing means pressing said press member on said body surface with a predetermined constant pressing force during said outward advance of said first press surface from said second press surface for the determination of said optimum outward advance amount of said first press surface.

2. The apparatus according to claim 1, further comprising:

adjusting means for determining a pulse rate of said subject by utilizing the electric signal generated from said pressure sensing means and adjusting, by utilizing said pulse rate, a rate of said outward advance of said first press surface for the determination of said optimum outward advance amount.

3. The apparatus according to claim 2, wherein said adjusting means determines as said pulse rate a time duration, t, of a pulse of said pressure pulse wave represented by said electric signal from said pressure sensing means, and adjusts said outward advance rate to a value, a/t (a; constant).

4. The apparatus according to claim 2, wherein said adjusting means determines as said pulse rate a time duration, t, of each of pulses of said pressure pulse wave detected through said pressure sensing means during said outward advance of said first press surface for the determination of said optimum advance amount, and adjusts said outward advance rate to a value, a/t (a; constant), for detecting the pulse following said each pulse.

5. The apparatus according to claim 1, wherein said determining means (a) collects the electric signal corresponding to a plurality of pulses of said pressure pulse wave while said first press surface is advanced outward from said second press surface; (b) determines a lower peak magnitude and an amplitude of each of said pulses; (c) determines a first range of said outward advance amount of said first press surface in which range a change of said amplitude with respect to said outward advance amount is within a first predetermined value and which range contains an advance amount at which said pressure sensing means has detected a pulse having a maximum amplitude of the amplitudes of said pulses, and a second range of said outward advance amount in which range a change of said lower peak magnitude with respect to said outward advance amount is within a second predetermined value; and (d) determines said optimum outward advance amount based on said first and second ranges.

6. The apparatus according to claim 5, wherein said determining means determines as said optimum outward advance amount (a) an outward advance amount corresponding to the middle point of said second range in the case where said first range contains said second range in entirety thereof; (b), in the case where said first and second ranges partially overlap each other, an outward advance amount corresponding to the middle point of the overlapping portions of said first and second ranges; and (c) an outward advance amount corresponding to the middle point of said first range in the case where said second range contains said first range in entirety thereof or in the case where said first and second ranges are separate from each other.

7. The apparatus according to claim 1, wherein said determining means (a) collects the electric signal corresponding to a plurality of pulses of said pressure pulse wave while said first press surface is advanced outward from said second press surface; (b) determines an amplitude of each of said pulses; and (c) determines as said optimum outward advance amount an outward advance amount at which said pressure sensing means has detected a pulse having a maximum amplitude of the amplitudes of said pulses.

8. The apparatus according to claim 1, wherein said actuating means ceases advancing said first press surface upon determination of said optimum outward advance amount.

9. The apparatus according to claim 1, wherein said pressure sensing means comprises a plurality of pressure sensing elements each of which detects said pressure pulse wave and generates an electric signal representing the detected pressure pulse wave, said determining means determining an amplitude of each of pulses of the pressure pulse wave detected through said each pressure sensing element, selecting as an optimum pressure sensing element one of said pressure sensing elements which has detected a pulse having a maximum amplitude of the amplitudes determined for said elements, and determining said optimum advance amount by utilizing the electric signal supplied from said optimum pressure sensing element.

10. The apparatus according to claim 1, further comprising blood pressure determining means for identifying an upper and a lower peak of each of pulses of said pressure pulse wave represented by said electric signal from said pressure sensing means, and determining a systolic and a diastolic blood pressure of said subject based on the identified upper and lower peaks, respectively, for said each pulse.

11. The apparatus according to claim 10, further comprising displaying means for indicating a waveform of said pressure pulse wave detected by said pressure sensing means, and the systolic and diastolic blood pressure values determined by said blood pressure determining means.

12. The apparatus according to claim 1, wherein said actuating means comprising:
means for defining a fluid chamber; and
means for supplying said fluid chamber with a pressurized, non-compressible fluid for displacing said first press portion relative to said second press portion.

13. The apparatus according to claim 1, wherein said pressing means comprises:
a support member having an inner space; and
an elastic diaphragm secured to an inner surface of said support member, such that said elastic diaphragm cooperates with said support member to define a fluid chamber in said inner space of said support member.
said first and second press members being supported by one of opposite surfaces of said elastic diaphragm which one surface is remote from the other surface of said diaphragm defining said fluid chamber.

14. The apparatus according to claim 13, further comprising air supply means for supplying said fluid chamber with a pressurized air.

15. The apparatus according to claim 13, further comprising drive means for displacing said support member relative to said housing in a direction intersecting a direction in which said arterial vessel of said subject extends.

16. An apparatus for detecting a pressure pulse wave produced from an arterial vessel of a living subject, comprising:
a first press member having a first press surface;
pressure sensing means supported by said first press surface;
a second press member having a second press surface surrounding said first press surface;
pressing means for pressing said first and second press members toward a body surface of said subject so that said first press surface is pressed against said arterial vessel of said subject via said body surface;
said pressure sensing means generating an electric signal representing said pressure pulse wave produced from said arterial vessel and transmitted thereto via said body surface;
said first and second press member being displaceable relative to each other in a direction in which the first and second press members are pressed by said pressing means;
actuating means for displacing said first press member relative to said second press member so that said first press surface is advanced outward from said second press surface;

determining means for determining an optimum amount of the outward advance of said first press surface from said second press surface, by utilizing the electric signal generated from said pressure sensing means when said first press member is displaced outward from said second press member by said actuating means with the second press member being pressed on said body surface by said pressing means; and adjusting means for determining a pulse rate of said subject by utilizing the electric signal generated from said pressure sensing means and adjusting, by utilizing said pulse rate, a rate of said outward advance of said first press surface for the determination of said optimum outward advance amount.

17. The apparatus according to claim 16, wherein said adjusting means determines as said pulse rate a time duration, t, of a pulse of said pressure pulse wave represented by said electric signal from said pressure sensing means, and adjusts said outward advance rate to a value, a/t (a; constant).

18. The apparatus according to claim 16, wherein said adjusting means determines as said pulse rate a time duration, t, of each of pulse of said pressure pulse wave detected through said pressure sensing means during said outward advance of said first press surface for the determination of said optimum advance amount, and adjusts said outward advance rate to a value, a/t (a; constant), for detecting the pulse following said each pulse.

19. An apparatus for detecting a pressure pulse wave produced from an arterial vessel of a living subject, comprising:

a first press member having a first press surface;
pressure sensing means supported by said first press surface;
a second press member having a second press surface surrounding said first press surface;
pressing means for pressing said first and second press members toward a body surface of said subject so that said first press surface is pressed against said arterial vessel of said subject via said body surface;
said pressure sensing means generating an electric signal representing said pressure pulse wave produced from said arterial vessel and transmitted thereto via said body surface;
said first and second press member being displaceable relative to each other in a direction in which the first and second press members are pressed by said pressing means;
actuating means for displacing said first press member relative to said second press member so that said first pressure surface is advanced outward from said second press surface; and
determining means for determining an optimum amount of the outward advance of said first press surface from said second press surface, by utilizing the electric signal generated from said pressure sensing means when said first press member is displaced outward from said second press member by said actuating means with the second press member being pressed on said body surface by said pressing means, wherein said determining means (a) collects the electric signal corresponding to a plurality of pulses of said pressure pulse wave while said first press surface is advanced outward from said second press surface; (b) determines a lower peak magnitude and an amplitude of each of said pulses; (c) determines a first range of said outward advance amount of said first press surface in which range a change of amplitude with respect to said outward advance amount is within a first predetermined value and which range contains an advance amount at which said pressure sensing means has detected a pulse having a maximum amplitude of the amplitudes of said pulses, and a second range of said outward advance amount of in which range a change of said lower peak magnitude with respect to said outward advance amount is within a second predetermined value; and (d) determines said optimum outward advance amount based on said first and second ranges.

20. The apparatus according to claim 19, wherein said determining means determines as said optimum outward advance amount (a) an outward advance amount corresponding to the middle point of said second range in the case where said first range contains said second range in entirety thereof; (b), in the case where said first and second ranges partially overlap each other, an outward advance amount corresponding to the middle point of the overlapping portions of said first and second range; and (c) an outward advance amount corresponding to the middle point of said first range in the case where said second range contains said first range in entirety thereof or in the case where said first and second ranges are separate from each other.

* * * * *